United States Patent
Aldritt et al.

(10) Patent No.: US 8,168,240 B2
(45) Date of Patent: *May 1, 2012

(54) EFFERVESCENT COMPOSITION INCLUDING CRANBERRY EXTRACT

(75) Inventors: Mary Aldritt, Excelsior, MN (US);
Robert E Lee, St. Louis Park, MN (US);
Fred Wehling, Greenfield, MN (US)

(73) Assignee: Amerilab Technologies, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/843,678

(22) Filed: Jul. 26, 2010

(65) Prior Publication Data

US 2010/0285158 A1   Nov. 11, 2010

Related U.S. Application Data

(63) Continuation of application No. 10/759,892, filed on Jan. 16, 2004, now Pat. No. 7,785,640.

(51) Int. Cl.
*A61K 36/45* (2006.01)
(52) U.S. Cl. ........................................ 424/732; 424/466
(58) Field of Classification Search ........................ None
See application file for complete search history.

(56) References Cited

U.S. PATENT DOCUMENTS

| | | | | |
|---|---|---|---|---|
| 4,704,269 | A | * | 11/1987 | Korab .............................. 424/44 |
| 5,223,264 | A | * | 6/1993 | Wehling et al. ................ 424/466 |
| 7,785,640 | B2 | * | 8/2010 | Aldritt et al. ................... 424/732 |
| 2002/0102336 | A1 | * | 8/2002 | Mann ............................ 426/321 |

FOREIGN PATENT DOCUMENTS

| | | | |
|---|---|---|---|
| AU | 200157788 A1 | * | 2/2002 |
| CN | 1211189 | | 3/1999 |
| JP | 2001-342142 | * | 12/2001 |
| WO | WO9729763 | | 8/1997 |

OTHER PUBLICATIONS

Lieberman et al. eds. (Pharmaceutical Dosage Forms: Tablets. Second Edition, vol. 1. New York: Marcel Dekker, Inc. 1989. pp. 285-303).*

* cited by examiner

*Primary Examiner* — Susan Hoffman
(74) *Attorney, Agent, or Firm* — Allison Johnson; Allison Johnson, P.A.

(57) ABSTRACT

Disclosed is an effervescent composition that includes an effervescent agent and cranberry extract, preferably in an amount sufficient to decrease the measurable amount of bacteria present in the urine of an individual having a urinary tract infection.

18 Claims, No Drawings

EFFERVESCENT COMPOSITION INCLUDING CRANBERRY EXTRACT

CROSS REFERENCE TO RELATED APPLICATIONS

This application is a continuing application of U.S. patent application Ser. No. 10/759,892, filed Jan. 16, 2004, now U.S. Pat. No. 7,785,640, and incorporated herein by reference.

BACKGROUND

The invention relates to effervescent compositions that include cranberry extract.

Cranberries, which include flavonoids (e.g., anthocyanins, flavonols and proanthocyanidins), hydroxycinnamic acids, phenols, polyphenols, omega-3 fatty acids, and omega-6 fatty acids, have been noted for their potential health benefits. Cranberry juice, for example, is often recommended for use in the treatment of urinary tract infections. The term "urinary tract infection" is used to refer to a variety of conditions including cystitis (infection of the bladder), pyelonephutis (infection of the kidney), and urethritis (infection of the urethra). Various studies have shown that cranberry juice, and in particular the proanthocyanidins present in cranberries, inhibit bacteria such as *Escherichia coli* (*E. coli*) from attaching to and colonizing on the walls of the urinary tract. One such study showed that elderly women who consumed ten ounces a day of a commercial cranberry juice cocktail showed a reduction in the level of bacteria and white blood cell count in their urine.

Cranberries have also been noted for their relatively high antioxidant content. Antioxidants have been highlighted as disease fighters.

In general, cranberry juice is commercially available to a user in a bottled form that usually contains multiple servings. At times, such bottles can be rather inconvenient dosage forms and may not be readily available. In addition, many commercially available cranberry juices are not 100% juice, as they often include sweeteners and other additives. In most commercially available cranberry juices only a fraction of the juice that is present in the product is cranberry juice.

Various efforts have been made to provide the beneficial effects of cranberries to individuals in a convenient and more concentrated form. One such effort involved the development of tablets of concentrated cranberry juice. Another effort involved the development of a time-release capsule for delivering extracts of cranberries to the body over time.

Various problems can arise when attempting to mass-produce tablets including picking, die wall etching, capping and laminating. "Picking" refers to the phenomenon that occurs when a portion of the tablet composition sticks to one or more faces of the punches used to form the tablets. In mass producing tablets, the die of the tablet press is filled with the effervescent composition, two opposing faces of the die punch of the tablet press come together to compress the composition and form the tablet, and then the tablet is ejected from the die. It is the two punch faces to which the "picked" composition sticks after the tablets are ejected from the die punch. Picking is also evidenced by the presence of indentations on the surface of the tablet (i.e., the face of the tablet).

"Die wall etching" refers to the phenomenon that occurs when the tablet composition sticks to or builds up on the side walls of the tablet. Die wall etching is evidenced by the presence of scratches or lines on the side walls of the tablet.

"Capping" refers to the splitting off of the top surface of the tablet from the body of the tablet.

"Lamination" refers to the presence of definite striations or layers within the tablet that are visible when the tablet is broken in half. When lamination occurs, the tablet often splits and comes apart at the sides during the tableting operation and is ejected from the die in two parts.

SUMMARY

In one aspect, the invention features a tablet that includes an effervescent composition that includes at least 200 mg cranberry extract, an effervescent agent that includes an acid and a base, binder, and lubricant, wherein the tablet disintegrates in water in less than 2.5 minutes. In one embodiment, the cranberry extract includes cranberry oil.

In another embodiment, the cranberry extract is a water soluble cranberry extract powder. In some embodiments, the cranberry extract includes proanthocyanidins. In one embodiment, the tablet includes at least 500 mg cranberry extract. In other embodiments, the tablet includes from about 750 mg to about 1500 mg cranberry extract. In some embodiments, the tablet includes about 1000 mg cranberry extract. In another embodiment, the tablet includes at least 2% by weight cranberry extract. In some embodiments, the tablet includes from 10% by weight to 35% by weight cranberry extract. In one embodiment, the tablet dissolves in less than 2 minutes.

In another embodiment, the effervescent agent includes sodium bicarbonate and citric acid, the tablet further that includes polyethylene glycol, sorbitol and sodium benzoate. In some embodiments, the tablet includes from 20% by weight to 25% by weight sorbitol.

In other embodiments, the tablet further includes magnesium hydroxide.

In another embodiment, the tablet further includes cranberry flavoring agent different from the cranberry extract.

In one embodiment, the tablet dissolves in excess water to form a composition that is free of surface scum.

In other embodiments, the tablet includes an effervescent composition that includes from 50 mg to 200 mg cranberry seed oil, and an effervescent agent that includes an acid and a base, the tablet having a hardness of at least 5 kilopounds and disintegrating in water less than 2.5 minutes.

In some embodiments, the tablet includes an effervescent composition that includes cranberry extract in an amount sufficient to measurably decrease the amount of bacteria present in the urine of an individual having a urinary tract infection, an effervescent agent, binder, and lubricant.

In one embodiment, the amount of cranberry extract is sufficient to measurably decrease the amount of *Escherichia coli* present in the urine of an individual having a urinary tract infection. In another embodiment, the tablet further includes magnesium hydroxide.

In other aspects, the invention features a method of treating an individual with a urinary tract infection, the method that includes disintegrating the effervescent tablet of claim 1 in at least 200 mL of water, and orally administering the resulting composition to the individual.

In another aspect, the invention features a method of mass producing multiple effervescent tablets, the method that includes filling a plurality of dies of a tablet press with an effervescent composition that includes at least 200 mg cranberry extract, an effervescent agent that includes an acid and a base, binder, and lubricant, and compressing the effervescent composition between two faces of a punch to form a tablet in each die having a hardness of at least 5 Kp, and ejecting the tablets from the dies. In one embodiment, the method further includes sealing individual ones of the tablets in a packaging material to form an airtight sealed package. In another embodiment, the method further includes drying the cranberry extract prior to combining the cranberry extract with the effervescent agent.

In other embodiments, the packaging material includes a metal foil pouch. In some embodiments, the packaging material is a blister pack.

In another embodiment, the tablets are free of picking, capping, and die wall etching.

In other embodiments, the cranberry extract includes cranberry oil, and the method further that includes combining the cranberry oil and the base to form a mixture, and combining the mixture with the binder and the lubricant.

The present invention provides an effervescent composition that disintegrates rapidly, preferably forms a clear solution that is free of surface scum, and provides a palatable and visually pleasing source of cranberry extract for ingestion by a user. The effervescent composition can be formulated to include a therapeutically effective amount of cranberry extract and can be used to treat an individual suffering from a urinary tract infection.

The invention also features an effervescent composition that can be used in a tablet mass production operation to produce tablets that are free from the effects of picking, die wall etching, capping, and lamination.

Other features and advantages will be apparent from the following description of the preferred embodiments and from the claims.

GLOSSARY

In reference to the invention, these terms have the meanings set forth below:

The term "effervescent composition" refers to a composition that gives off gas (e.g., carbon dioxide) bubbles when placed in an aqueous liquid.

DETAILED DESCRIPTION

The effervescent composition includes an effervescent agent and cranberry extract. The composition preferably includes cranberry extract in an amount sufficient to provide a therapeutic effect to an individual suffering from a urinary tract infection. By therapeutic effect it is meant an amount that will measurably decrease the amount of one or more strains of bacteria, e.g., E. coli, detected in the urine of an individual having a urinary tract infection. Preferably the cranberry extract is present in the composition in an amount of at least 200 mg, at least 300 mg, at least 500 mg, from 500 mg to 2000 mg, from 500 mg to 1500 mg, from 750 mg to 1500 mg, or even about 1000 mg per dosage unit. Other useful compositions include cranberry extract in an amount of at least about 2% by weight, from about 3% by weight to about 50% by weight, from about 10% by weight to about 35% by weight cranberry extract, or even 15% by weight to 30% by weight.

The cranberry extract can exist in a variety of forms including, e.g., powder, coated powder, and oil. Preferably the cranberry extract is a water soluble powder. Useful cranberry extracts are available, e.g., under the trade designation Cranberry 90MX Powder from Ocean Spray Technology Group (Middleboro, Mass.), under the trade designation CRAN-MAX from Cape Cod Biolab Corporation (Buzzards Bay, Mass.), and Future*Ceutical HiActives cranberry powder from Van Drunen Farms (Santa Rosa, Calif.). One suitable source of cranberry oil is cranberry seed oil available from Badger Oil Company (Spooner, Wis.). The cranberry extract can include an agent (e.g., magnesium hydroxide) that enhances the flow of the powdered extract.

The effervescent composition is water soluble and rapidly disintegrates. Preferably the effervescent composition dissolves to a clear solution when placed in excess water at room temperature (about 22° C.) in less than 2.5 minutes, or even in less than 2 minutes. The uniformity and clarity of the composition is determined by viewing with the naked eye. The composition preferably is self-mixing, i.e., when excess water is added to the effervescent composition, the effervescent composition will dissolve on its own without mixing or stirring from another source. The composition is palatable, can be easily swallowed and has a pH from 3 to 5.

The effervescent composition is stable. Preferably the effervescent composition, when stored at 40° C. and 75% relative humidity in a sealed, air tight, moisture proof package, the package exhibits minimal visible puffing, or even is free of visible puffing for a period of at least 7 days, 14 days, or even 4 weeks.

The effervescent agent is preferably an effervescent couple that includes an acid and a base. The effervescent agent is activated when contacted with water, e.g., when the powder or tablet is placed in a glass of water. The water liberates the acid and base and enables the acid and base to react with each other to produce carbon dioxide gas, which imparts carbonation to the aqueous composition. Examples of useful acids include citric acid, ascorbic acid, aspartic acid, malic acid, adipic acid, tartaric acid, fumaric acid, succinic acid, sodium acid pyrophosphate, lactic acid, hexamic acid, amino acids, and acid salts and acid anhydrides thereof, and mixtures thereof. Examples of useful acid anhydrides include citraconic anhydride, glucono-D-lactone, and succinic anhydride. Examples of useful acid salts include potassium bitartrate, acid citrate salts, sodium dihydrogen phosphate, disodium dihydrogen phosphate, sodium acid sulfite, and combinations thereof. Preferably acid is present in the composition in an amount of from 10% by weight to about 60% by weight, from about 15% by weight to about 50% by weight, or even from about 25% by weight to about 40% by weight.

The base preferably is capable of generating a gas such as carbon dioxide. Examples of suitable carbonate bases include sodium bicarbonate, sodium carbonate, sodium sesquicarbonate, potassium carbonate, potassium bicarbonate, calcium carbonate, magnesium carbonate, magnesium oxide, sodium glycine carbonate, L-lysine carbonate, arginine carbonate, zinc carbonate, zinc oxide, amino acid carbonates, and mixtures thereof. The composition preferably includes base in an amount of from 10% by weight to about 60% by weight, from about 15% by weight to about 50% by weight, or even from about 25% by weight to about 40% by weight.

The effervescent composition can optionally include a variety of additional active agents including, e.g., vitamins, amino acids, pharmaceutical agents, minerals, dietary supplements, and combinations thereof. Suitable vitamins include, e.g., ascorbic acid (vitamin C), aspartic acid, thiamin, riboflavin, nicotinic acid, pantothenic acid, pyridoxine, biotin, folic acid, niacin, vitamin B12, lipoic acid, vitamin A, vitamin D, vitamin E and vitamin K and coenzymes thereof, choline, carnitine, and alpha, beta, and gamma carotenes. Examples of coenzymes include thiamine pyrophosphates, flavin mononucleotide, flavin adenine dinucleotide, nicotinamide adenine dinucleotide, nicotinamide adenine dinucleotide phosphate coenzyme A pyridoxal phosphate, biocytin, tetrahydrofolic acid, coenzyme B12, lipoyllysine, 11-cis-retinal, and 1,25-dihydroxycholecalciferol and mixtures.

Suitable amino acids include, e.g., L-tyrosine, isoleucine, ornithine, glutamine, phenylalanine, leucine, lysine, methionine, threonine, taurine, tryptophan, valine, alanine, glycine, arginine, histidine, cysteine, asparagine, proline and serine, and mixtures thereof.

Examples of minerals include iron, zinc, selenium, copper, iodine, phosphorus, chromium and mixtures thereof.

Suitable dietary supplements include, e.g., bee pollen, bran, wheat germ, kelp, cod liver oil, ginseng, and fish oils, amino-acids, proteins, vitamins, minerals alpha-glycerylphosphorylcholine, acetyl-L-carnitine and salts thereof, docosahexaenoic acid, cranberry extract, chondroitin, methylsulfonylmethane, and mixtures thereof.

The composition can also include other ingredients including, e.g., flavor agents, fillers, surfactants (e.g., polysorbate 80 and sodium lauryl sulfate), color agents including, e.g., dyes and pigments, sweeteners, and flow agents.

The cranberry extract can provide flavoring to the effervescent composition. In addition, other useful flavor agents include natural and artificial flavoring agents including, e.g., volatile oils, synthetic flavor oils, flavoring aromatics, oils, liquids, oleoresins and extracts derived from plants, leaves, flowers, fruits, stems and combinations thereof. Useful flavor agents include, e.g., citric oils, e.g., lemon, orange, grape, lime and grapefruit, fruit essences including, e.g., apple, pear, peach, grape, strawberry, raspberry, cherry, plum, pineapple, apricot, and other fruit flavors. Other useful flavor agents include, e.g., aldehydes and esters (e.g., benzaldehyde (cherry, almond)), citral, i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), 2-dodedenal (citrus, mandarin) and mixtures thereof.

Useful color agents include, e.g., food, drug and cosmetic (FD&C) colors including, e.g., dyes, lakes, and certain natural and derived colorants. Useful lakes include dyes absorbed on aluminum hydroxide and other suitable carriers.

Useful sweetening agents include stevia, sugars such as sucrose, glucose, invert sugar, fructose, ribose, tagalose, sucralose, malitol, erythritol, xylitol, and mixtures thereof, saccharin and its various salts (e.g., sodium and calcium salt of saccharin), cyclamic acid and its various salts, dipeptide sweeteners (e.g., aspartame), acesulfame potassium, dihydrochalcone, glycyrrhizin, and sugar alcohols including, e.g., sorbitol, sorbitol syrup, mannitol and xylitol, and combinations thereof.

The effervescent composition can be provided in a variety of forms including, e.g., powder (e.g., a free flowing granulation), tablet, capsule, pellet and composite. Preferred effervescent tablets have a hardness of at least 3 kilopounds (Kp), preferably at least 5 Kp, from about 5 Kp to about 10 Kp, or even from about 5 Kp to about 8 Kp, as measured on a standard hardness tester fitted with a strain gauge.

When in the form of a tablet, the composition preferably includes binder, lubricant, and combinations thereof. Examples of suitable binders include, e.g., starches, natural gums, cellulose gums, microcrystalline cellulose, methylcellulose, cellulose ethers, sodium carboxymethylcellulose, ethylcellulose, gelatin, dextrose, lactose, sucrose, sorbitol, mannitol, polyethylene glycol, polyvinylpyrrolidone, pectins, alginates, polyacrylamides, polyvinyloxoazolidone, polyvinylalcohols and mixtures thereof. Preferably the binder is water soluble.

Where present, the composition includes a sufficient amount of binder to assist in holding the components of the composition together in the form of a tablet. When present, the composition preferably includes binder in an amount from 10% by weight to about 60% by weight, from about 15% by weight to about 50% by weight, or even from about 20% by weight to about 40% by weight, or even 20% by weight to 30% by weight.

Various lubricants are suitable for use in the composition including water dispersible, water soluble, water insoluble lubricants and combinations thereof. Preferred lubricants are water soluble. Some lubricants also provide a binder function and vice versa. Examples of useful water soluble lubricants include sodium benzoate, polyethylene glycol, L-leucine, adipic acid, and combinations thereof. The composition can also include water insoluble lubricants including, e.g., stearates (e.g., magnesium stearate, calcium stearate and zinc stearate), oils (e.g., mineral oil, hydrogenated and partially hydrogenated vegetable oils, and cotton seed oil) and combinations thereof. Other water insoluble lubricants include, e.g., animal fats, polyoxyethylene monostearate, talc, and combinations thereof.

The composition preferably includes a sufficient amount of lubricant to enable the composition to be formed into tablets and released from a high speed tableting press in the form of a tablet. When present, the composition preferably includes lubricant in an amount of from 1% by weight to about 15% by weight, from about 1% by weight to about 12% by weight, from about 2% by weight to about 10% by weight, or even from about 3% by weight to about 8% by weight.

The effervescent composition is preferably stored in a moisture-proof package including, e.g., sealed metal foil pouches, blister packs, and desiccant capped tubes. Useful packaging materials further include metal foil, plastic films, and blister packaging.

The composition can be administered by dissolving the composition in excess water, e.g., an eight ounce glass of tap water, to form an aqueous solution and ingested. After addition of the effervescent composition to an aqueous liquid, the composition optionally can be stirred to facilitate dispersion and/or dissolution in the aqueous liquid.

The effervescent composition for tableting is well suited to the mass production of effervescent tablets that are free from picking, die wall etching, capping and lamination. Any suitable tablet mass production equipment and processes can be used. Examples of useful tableting processes for effervescent compositions are described in *Pharmaceutical Dosage Forms: Tablets*, Volume 1, Lieberman, $2^{nd}$ ed. 1989. The components of the effervescent composition are preferably dried prior to formulating. The tablets can then be manufactured in an automated process in which multiple dies of a tablet press are filled sequentially or simultaneously with the effervescent composition, two punches compress the effervescent composition to form the tablet(s), and then the tablet (s) is ejected from the die. The tablets preferably vary in weight by no more than +/−2.5%. The tablet is then placed in packaging material, which is then sealed to form an air tight sealed package. The packaged tablet can be further processed by conveying it to other processing stations including, e.g., additional packaging stations for further packaging, e.g., boxing and bagging.

The tablet manufacturing and initial packing operations are preferably preformed in a controlled environment in which the temperature and humidity are controlled. Preferably the controlled environment has less than 18 grains, less than 16 grains, or even less than 15 grains of moisture.

The invention will now be described by way of the following examples.

EXAMPLES

Example 1

An effervescent composition was prepared by combining the following ingredients with mixing: 900 mg citric acid, 300 mg sodium bicarbonate, 100 mg sodium carbonate grade 50, 500 mg sorbitol instant, 150 mg polyethylene glycol 3350, 90 mg sodium benzoate, 1000 mg Cranberry 90MX cranberry extract (Ocean Spray, Lakeville-Middleboro, Mass.), 500 mg ascorbic acid, 35 mg artificial cranberry flavoring agent (SD #705K) (Virginia Dare, Brooklyn, N.Y.), 30 mg aspartame, and 15 mg acesulfame k.

The composition was then placed in 200 ml water and was observed to dissolve to a clear solution. The taste of the solution was similar to commercial cranberry juices.

Example 2

An effervescent composition was prepared by passing the solid ingredients listed below through a number 12 sieve, with the exception of the sodium carbonate, which was passed through a number 20 sieve, prior to combining the ingredients with mixing in a mixer for five minutes on low speed: 1350 mg citric acid, 700 mg sodium bicarbonate, 100 mg sodium carbonate grade 50, 750 mg sorbitol instant, 170 mg polyethylene glycol 3350, 100 mg sodium benzoate, 500 mg CRAN-MAX cranberry extract, 35 mg artificial cranberry flavoring agent (SD #705K), 30 mg aspartame, and 15 mg acesulfame k.

The composition was then placed in 200 ml water, whereupon it disintegrated. The taste of the resulting composition was similar to commercial cranberry juices. Initially there were red granules suspended in the water but eventually the granules fell to the bottom of the vessel. The CRAN-MAX extract was observed to be insoluble in 200 ml of water.

The composition did not form tablets. Picking was present on the punch faces.

Example 3

The following ingredients were passed through a number 12 sieve, with the exception of the sodium carbonate, which was passed through a number 20 sieve, prior to combining with mixing in a mixer for five minutes on low speed: 1350 mg citric acid, 700 mg sodium bicarbonate, 100 mg sodium carbonate grade 50, 1000 mg sorbitol instant, 200 mg polyethylene glycol 3350, 125 mg sodium benzoate, 500 mg CRAN-MAX cranberry extract, 35 mg artificial cranberry flavoring agent (SD #705K), 30 mg aspartame, and 15 mg acesulfame k. The composition was formed into 1 inch diameter tablets having a thickness of about 0.25 inch, an average weight of about 4 g, and an average hardness of about 6 Kp. Slight picking was observed on the lower punches of the tablet press; however, the appearance of the tablets was not compromised. No die wall etching was observed. Capping occurred at 6.4 Kp.

A tablet was placed in 200 ml water and observed to dissolve almost completely in 84 seconds. The color of the resulting composition was redish pink. Granules were visible and settled to the bottom of the vessel. Taste was similar to commercial cranberry juices. Initially there were red granules suspended in the water but eventually the granules fell to the bottom of the vessel.

Example 4

The following ingredients were passed through a number 12 sieve, with the exception of the sodium carbonate, which was passed through a number 20 sieve, prior to combining with mixing in a mixer for five minutes on low speed: 1350 mg citric acid, 700 mg sodium bicarbonate, 100 mg sodium carbonate grade 50, 1000 mg sorbitol instant, 200 mg polyethylene glycol 3350, 125 mg sodium benzoate, 1000 mg 90MX cranberry extract (Ocean Spray), 35 mg artificial cranberry flavoring agent (SD #705K), 30 mg aspartame, and 15 mg acesulfame k. The composition was formed into 1 inch diameter tablets having a thickness of about 0.28 inch, an average weight of about 4.5 g, and an average hardness of about 7.9 Kp. Slight picking was observed on the upper punches of the tablet press; however, the appearance of the tablets was not compromised. No die wall etching was observed.

A tablet was placed in 200 ml water and observed to dissolve almost completely in 211 seconds. The color of the resulting composition was a dark pink to light red. No granules were visible. The taste of the composition was similar to commercial cranberry juices.

Tablets were packaged in sealed, air tight metal foil pouches and stored at room temperature and 40° C. 75% relative humidity. The packages were examined after one week and four weeks and the results are set forth below in Table 1.

TABLE 1

| Storage Duration | Room Temperature | 40° C. 75% Relative Humidity |
| --- | --- | --- |
| 1 week | Minimal puffing in one of four samples | Minimal puffing. Slight tablet movement in the package |
| 4 weeks | No puffing. Slight tablet movement in one of two packages | Slight puffing in two of three packages |

Example 5

The following ingredients were passed through a number 12 sieve, with the exception of the cranberry seed oil, which was not sieved, prior to combining. The 35 mg cranberry seed oil (Badger Oil Company, Spooner, Wis.) and 700 mg sodium bicarbonate were mixed together in a mixing bowl for three minutes using a mixer. Then 1350 mg citric acid, 100 mg sodium carbonate grade 50, 725 mg sorbitol instant, 100 mg polyethylene glycol 3350, 35 mg artificial cranberry flavoring agent (SD #705K), 30 mg aspartame, and 15 mg acesulfame k were added to the mixing bowl and mixed. The composition was formed into 1 inch diameter tablets having a thickness of about 0.2 inch, an average weight of about 3.4 g, and an average hardness of about 4.5 Kp. The tablet was free of picking, die wall etching, capping and laminating.

A tablet was placed in 200 ml water and observed to dissolve in 113 seconds. The resulting composition was a solution that was slightly whitish/hazy in color with no particulates.

Example 6

The following ingredients were passed through a number 12 sieve, with the exception of the cranberry seed oil, which was not sieved, prior to combining with other ingredients. The 100 mg cranberry seed oil (Badger Oil Company) and 700 mg sodium bicarbonate were mixed together in a mixing bowl for five minutes using a mixer. Then 1350 mg citric acid, 100 mg sodium carbonate grade 50, 725 mg sorbitol instant, 100 mg polyethylene glycol 3350, 35 mg artificial cranberry flavoring agent (SD #705K), 30 mg aspartame, and 15 mg acesulfame k were added to the mixing bowl and mixed.

The composition was formed into 1 inch diameter tablets having a thickness of about 0.19 inch, an average weight of about 3.2 g, and an average hardness of about 3.4 Kp.

A tablet was placed in 200 ml water and dissolved in 80 seconds. The resulting composition had an oil layer on top and a more tart taste relative to the aqueous compositions formed from the tablets of Examples 1-5.

Tablets were packaged in sealed, air tight metal foil pouches and stored at room temperature and 40° C. 75% relative humidity. The packages were examined after four weeks and the results are set forth below in Table 2.

TABLE 2

| Storage Duration | Room Temperature | 40° C. 75% Relative Humidity |
| --- | --- | --- |
| 4 weeks | No puffing. No tablet movement. Tablet dissolved in 80 seconds. No taste degradation. | No puffing. Minimal tablet movement. Tablet dissolved in 70 seconds. No taste degradation. |

Other embodiments are within the claims.
What is claimed is:

1. An effervescent tablet comprising:
   from 10% by weight to 35% by weight cranberry extract comprising cranberry oil;
   an effervescent agent comprising an acid and a base;
   from 10% by weight to 60% by weight of the acid;
   from 10% by weight to 60% by weight of the base;
   from 10% by weight to 60% by weight binder; and
   from 1% by weight to 15% by weight lubricant,
   said tablet having a hardness of at least 5 kiloponds and disintegrating in water having a temperature of about 22° C. in less than 2.5 minutes.

2. The tablet of claim 1, wherein said cranberry extract further comprises a water soluble cranberry extract powder.

3. The tablet of claim 1, wherein said tablet comprises at least 500 mg cranberry extract.

4. The tablet of claim 1, wherein said tablet comprises from about 750 mg to about 1500 mg cranberry extract.

5. The tablet of claim 1, wherein said tablet comprises at least about 1000 mg cranberry extract.

6. The tablet of claim 1, wherein said tablet dissolves in less than 2 minutes.

7. The tablet of claim 1, wherein
   said base comprises sodium bicarbonate,
   said acid comprises citric acid,
   said binder comprises polyethylene glycol and sorbitol, and
   and said lubricant comprises sodium benzoate.

8. The tablet of claim 1, wherein said binder comprises sorbitol and said tablet comprises from 20% by weight to 25% by weight sorbitol.

9. The tablet of claim 1, wherein said tablet dissolves in water to form a composition that is free of surface scum.

10. The tablet of claim 1, further comprising magnesium hydroxide.

11. A method of treating an individual with a urinary tract infection, said method comprising:
   disintegrating the effervescent tablet of claim 1 in at least 200 mL of water; and
   orally administering the resulting composition to the individual.

12. A method of mass producing multiple effervescent tablets, said method comprising:
   filling a plurality of dies of a tablet press with an effervescent composition comprising
      from 10% by weight to 35% by weight cranberry extract comprising cranberry oil,
      an effervescent agent comprising an acid and a base,
      from 10% by weight to 60% by weight of the acid,
      from 10% by weight to 60% by weight of the base,
      from 10% by weight to 60% by weight binder, and
      1% by weight to 15% by weight lubricant;
   compressing said effervescent composition between two faces of a punch to form tablets having a hardness of at least 5 Kp; and
   ejecting said tablets from said die,
   said tablets disintegrating in water having a temperature of about 22° C. in less than 2.5 minutes.

13. The method of claim 12 further comprising sealing individual tablets in a packaging material to form an airtight sealed package.

14. The method of claim 12 further comprising drying said cranberry extract prior to combining said cranberry extract with said effervescent agent.

15. The method of claim 13, wherein said packaging material comprises at least one of a metal foil pouch and a blister pack.

16. The method of claim 12, wherein said tablets are free of picking, capping, and die wall etching.

17. The method of claim 12, wherein said cranberry extract further comprises a water soluble cranberry extract powder.

18. The method of claim 12 further comprising:
   combining said cranberry oil and said base to form a mixture; and
   combining said mixture with said binder and said lubricant.

* * * * *